(12) United States Patent
Kelly (10) Patent No.: US 8,136,529 B2
(45) Date of Patent: Mar. 20, 2012

(54) MANDIBULAR ADVANCEMENT DEVICE

(75) Inventor: Christopher William Kelly, Sydney (AU)

(73) Assignee: Be Well IP Pty Limited, Woollahra, New South Wales (AU)

( * ) Notice: Subject to any disclaimer, the term of this patent is extended or adjusted under 35 U.S.C. 154(b) by 265 days.

(21) Appl. No.: 12/513,923

(22) PCT Filed: Nov. 7, 2007

(86) PCT No.: PCT/AU2007/001702
§ 371 (c)(1),
(2), (4) Date: Jun. 4, 2009

(87) PCT Pub. No.: WO2008/055299
PCT Pub. Date: May 15, 2008

(65) Prior Publication Data
US 2010/0043805 A1    Feb. 25, 2010

(30) Foreign Application Priority Data

Nov. 7, 2006   (AU) ................................ 2006906169

(51) Int. Cl.
*A61F 5/56* (2006.01)
(52) U.S. Cl. ........................................................ 128/848
(58) Field of Classification Search ............... 433/6, 18, 433/19, 24, 37, 41, 68, 69, 140; 128/848
See application file for complete search history.

(56) References Cited

U.S. PATENT DOCUMENTS

| 4,901,737 | A  |   | 2/1990  | Toone |
| 5,683,244 | A  | * | 11/1997 | Truax ................................ 433/6 |
| 6,055,986 | A  | * | 5/2000  | Meade ........................... 128/848 |
| 6,604,527 | B1 | * | 8/2003  | Palmisano .................... 128/848 |
| 6,769,910 | B1 |   | 8/2004  | Pantino |
| 6,983,752 | B2 |   | 1/2006  | Garabadian |

FOREIGN PATENT DOCUMENTS

| EP | 1205157 | 5/2002 |
| FR | 2820307 | 8/2002 |
| WO | 2000001317 A1 | 1/2000 |

* cited by examiner

*Primary Examiner* — Patricia Bianco
*Assistant Examiner* — Raymond E Harris
(74) *Attorney, Agent, or Firm* — Novak Druce + Quigg LLP (57) ABSTRACT

A mandibular advancement device including upper and lower dental plates which operatively fit over at least part of the upper and lower teeth of a user, said upper and lower dental plates being made from a flexible material, the lower dental plate having two pairs of spaced apart pillars, each pair consisting of an anterior and posterior pillar, said pairs being on opposing sides of the lower dental plate, two removably attachable horizontal displacement inserts, mounted in the buccal region on opposite sides of the upper dental plate, two removably attachable vertical displacement inserts mounted in the lower dental plate, placed in a manner to provide correct vertical registration of the teeth, such that operatively each horizontal displacement insert is retained between the respective anterior and posterior pillars to maintain an advancement of the mandible. A method for production of the mandibular advancement device is also claimed.

11 Claims, 6 Drawing Sheets

Fig.1

Fig_2.

MANDIBULAR ADVANCEMENT DEVICE

FIELD OF THE INVENTION

This invention relates to a mandibular advancement device for reducing the incidence of sleep apnoea and other airway obstructive conditions.

BACKGROUND TO THE INVENTION

It is generally accepted that snoring and obstructive sleep apnoea occur when a sleeping person's tongue fully or partially blocks a constricted airway. Lifestyle changes, such as exercise and weight loss, are helpful in improving a constricted airway by reducing fat and increasing the muscle tone of the throat. However, this approach does not resolve the condition for all sufferers. Various devices and approaches to treating these conditions have been proposed.

Devices which move the mandible (lower jaw) forward and down from its habitual position relative to a patient's upper jaw also move the tongue forward and down in the mouth, and are consequently thought to reduce the likelihood of the tongue blocking or partially blocking the airway. Such devices are known as mandibular advancement devices.

One such device, disclosed in patent application WO 00/01317 by Palmisano, has an arrangement in which an upper and a lower dental plate are attached over a patient's lower and upper jaw. The plates define engaging sloping surfaces which are oriented such that as a patient's jaw closes, the engagement of the surfaces causes a patient's mandible to be advanced away from the habitual position relative to the upper jaw as the patient closes his jaw into the appliance.

The device described in WO 00/01317 has a number of disadvantages. In order to provide the requisite strength to make the device work, the upper and lower plates cover the incisal edges of the patient's teeth to enable the device to withstand the destructive forces of the mouth. In practice, the commercially available version of the device provided by Somnomed Limited is made with at least 2.5 mm thicknesses occlusally on both arches. This is a particular problem as it inhibits the patient's bite registration from being taken according to correct measured vertical guidelines. Also, the device is generally bulky, intrusive and relatively disturbing to patient comfort and thus encourages non-compliance by the patient (as patients do not like wearing uncomfortable devices). The hard material from which the commercially available device is made is uncomfortable to wear.

Other mandibular advancement devices are disclosed in which the upper and lower plates are connected to each other by extendable connectors, for example as is described in WO 95/19746. In such the devices, the connections intrude into the patient's oral cavity causing discomfort and thus encouraging non-compliance.

It is an object of the present invention to provide a mandibular advancement device that is effective in use while being more comfortable to wear.

SUMMARY OF THE INVENTION

Broadly, the present invention provides a device which is inserted when the mandible is placed into an advanced position, and functions to retain it in that position whilst allowing some degree of jaw movement. This permits the use of a less rigid device, and provides improved comfort to the user.

According to one aspect, the present invention provides a mandibular advancement device including upper and lower dental plates which operatively fit over at least part of the upper and lower teeth of a user, said upper and lower dental plates being made from a flexible material, the lower dental plate having two pairs of spaced apart pillars, each pair consisting of an anterior and posterior pillar, said pairs being on opposing sides of the lower dental plate, two removably attachable horizontal displacement inserts, mounted in the buccal region on opposite sides of the upper dental plate, two removably attachable vertical displacement inserts mounted in the lower dental plate, placed in a manner to provide correct vertical registration of the teeth, such that operatively each horizontal displacement insert is retained between the respective anterior and posterior pillars to maintain an advancement of the mandible.

According to another aspect, the present invention provides a mandibular advancement device, including upper and lower dental plates which operatively fit over at least part of the upper and lower teeth of a user, the lower and upper dental plates being formed as separate components, and being operatively resiliently retained together, the upper and lower plates including interoperating mechanical structures, such that operatively a predefined advancement of the mandible is retained by the device.

According to another aspect, the present invention provides a method of producing a mandibular advancement device, the method including at least the steps of:

(a) undertaking a consultation with the user, including taking impressions of the upper and lower teeth, and a measured bite registration;

(b) producing a model from the impressions:

(c) based upon said model, producing separate upper and lower plates, said plates being adapted to operatively fit over at least part of the upper and lower teeth of a user, the lower and upper dental plates being formed as separate components, the upper and lower plates including interoperating mechanical structures, such that the device is adapted to operatively maintain a predefined advancement of the mandible.

BRIEF DESCRIPTION OF THE DRAWINGS

An illustrative embodiment of the present invention will be described with reference to the accompanying figures, in which.

DETAILED DESCRIPTION

The present invention will be described principally with reference to a specific implementation. However, it will be understood that there are alternative structures and constructions which could be used to implement the present invention. The illustrative embodiment is intended to be illustrative of the present invention, but not limitative thereof.

Referring to the drawings, FIGS. 1 to 6 show a mandibular advancement device 10 embodying the present invention.

The device 10 includes an upper attachment member in the form of an upper dental plate 12, similar to a mouth guard, which fits over the teeth 11 of the upper jaw and a lower attachment member in the form of a lower dental plate 14 which fits over the teeth 13 of the mandible.

The upper 12 and lower plates 14 are moulded using a cast of the patient's mouth. It is preferred that the plates are made from a using a flexible permanently elastic resin. A commercially available product known as IVOCAP™ elastomer has been found to be particularly suitable. This elastomer is a heat cured methacrylate polymer with a suitable amount of plasticizers in it to make it extremely resilient and tear resistant. Further, it provides a safe, monomer free product when the plates 12,14 are completed.

The plates 12,14 are held in place on a patient's teeth 11,13 by retention forces due to the close fit but because the resin is flexible can easily be removed. The design of the plates is such that they are intended to be inserted by the patient in a particular way. The plates are connected by elastics (as will be explained further below), and the connected structure is fitted onto the teeth of the user with the mandible protruded to some extent. Once in place, the plates are retained in position, and in turn act to retain the mandible in the desired advanced position. As the structure is more concerned with retaining the advancement, rather than mechanically creating the advancement by some action between the plates, the structures are able to be less rigid and less intrusive into the patient's oral cavity.

Even though the biting surfaces of the teeth 11,13 may be covered, the plates 12,14 are not bulky. This conveys a feeling of open space to the patient because in a proprioceptive way they are perceiving space. The phonetic zone is over the rugae in the palate. Since the device does not cover this area at all patient compliance is optimised because they have no interference when drinking or licking their lips. Pro-proprioceptive influences cause one to purse one's lips and separate one's teeth just enough to get our tongue out to lick our lips. This is not possible with a thick layer of acrylic present over the top surfaces of the teeth.

Figure 5:
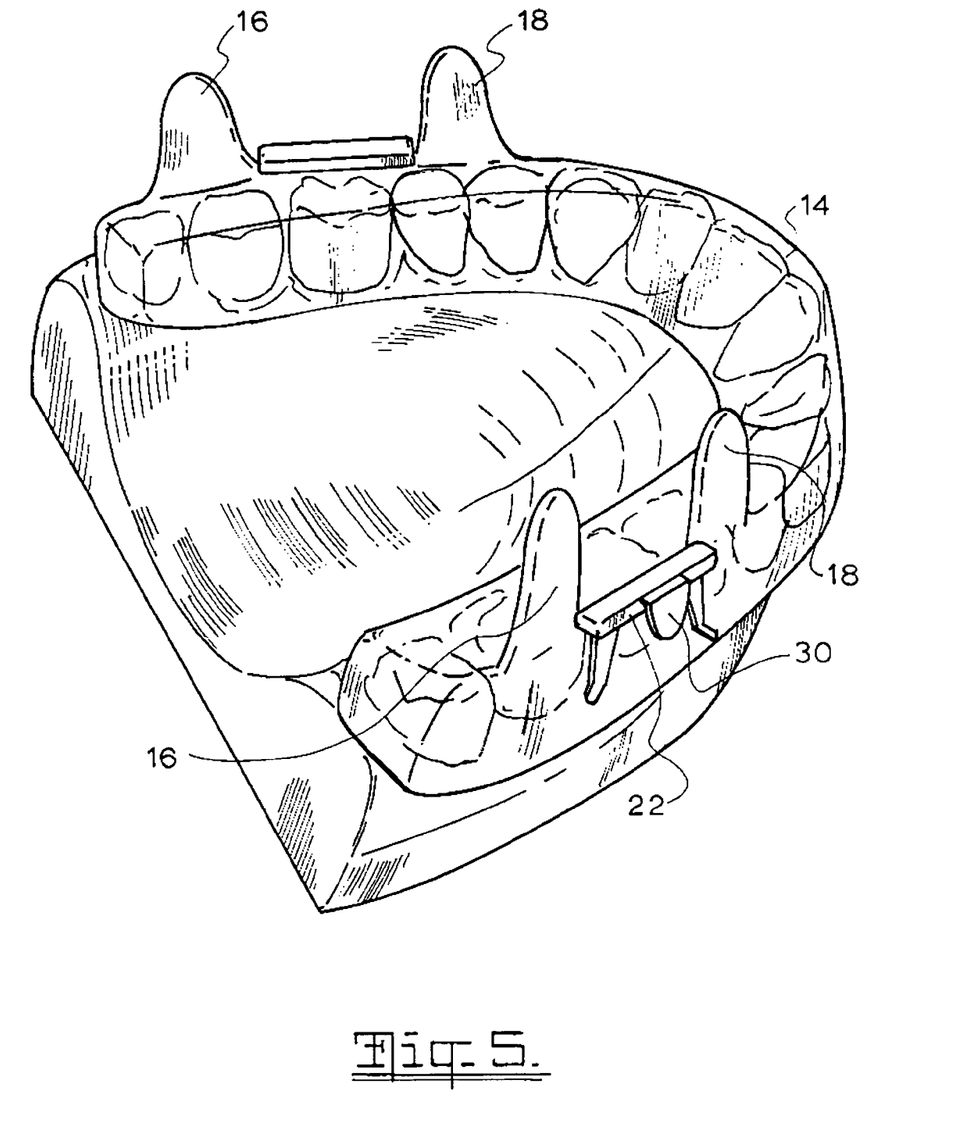
FIG. 5 is a view of an lower part of the device of FIG. 1.
Figure 6:
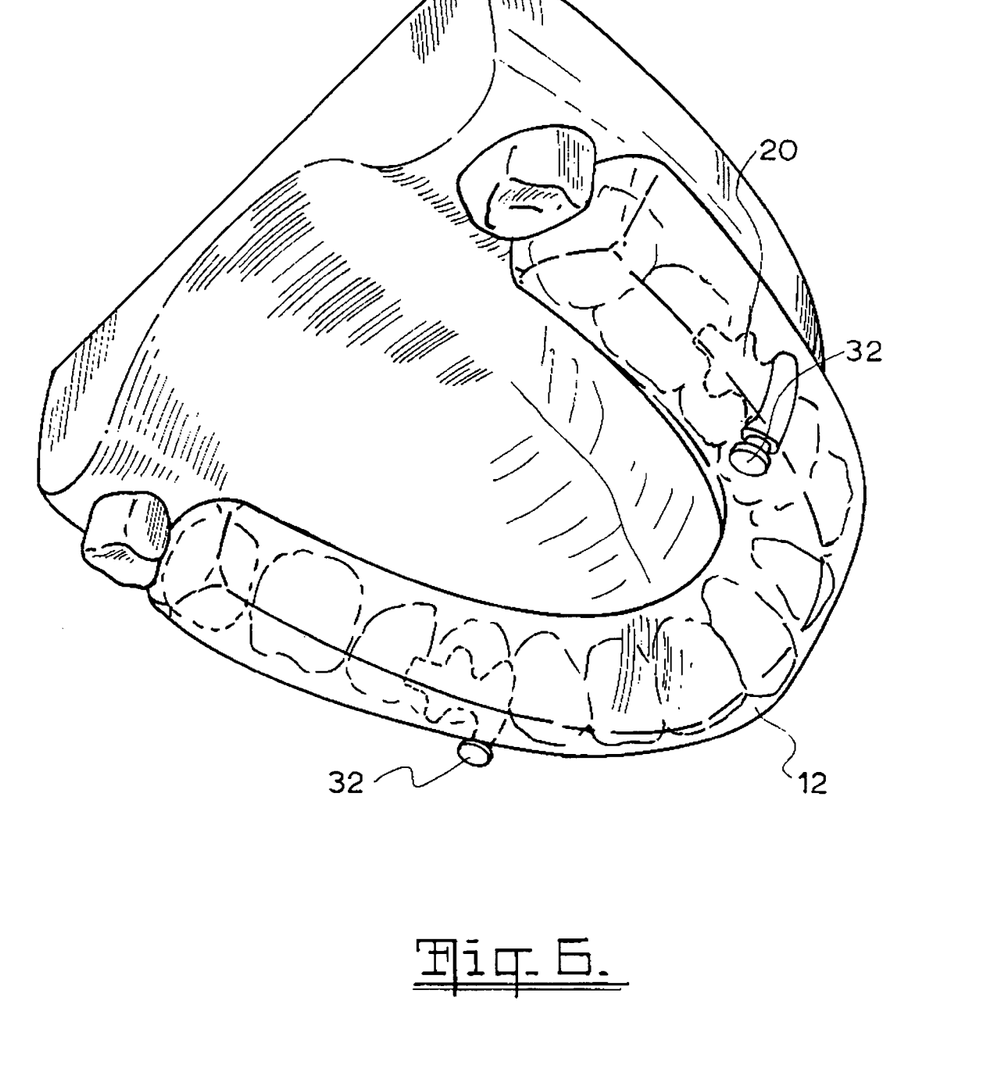
FIG. 6 is a view of an upper part of the device of FIG. 1.

The lower plate 14 includes a posterior 16 and an anterior pillar 18 on each side of the plate 14. These two spaced apart pillars 16, 18 project up from each side of the lower plate 14. The posterior pillar 16 is generally in the area of the posterior teeth and the anterior pillar 18 is positioned forward in the area of the pre-molars. A gap 18a, typically of the order of 2-3 cm or so across, is defined between each pair of pillars. The pillars act to retain the lower plate 14 and limit its movement relative to the upper plate, but the gap provides a degree of travel for the jaws relative to each other.

The upper plate 14 contains a processed void 12a on each buccal side. Within these voids 12a, removably attachable horizontal displacement inserts 20 are mounted. Insert 20 projects outwardly from each side of the upper plate 12. Insert 20 is mounted in processed void 12a so that its location on the upper buccal shield may be advanced or retruded to alter the lower jaw position relative to the upper jaw to position the patient's bite most optimally. Insert 20 may conveniently be supplied in preformed increments, for example of 1, 3, 5 and 7 mm. The tab typically has a width from 1.2 cm to 2 cm, and can best be seen in FIG. 6.

FIG. 5 shows the removably attachable and replaceable vertical insert 22 that sits in a processed void within the elastomer on the lower plate. This insert 22 allows the clinician to change the vertical movement of the patient's bite within the finished customised appliance 10. The insert 22 illustrated is a snap fit. Conveniently, insert 22 may be supplied as a pre-formed component with 1, 3, 5 and 7 mm increments, giving an available adjustment up to 7 mm for the clinician (as no insert, i.e. zero, is an option).

The inserts 20,22 are preferably formed from an injection moulded polypropylene of food grade quality, so that they can safely be used in devices and goods that are exposed to the oral environment. Of course, any other suitable material could be used.

Figure 1:
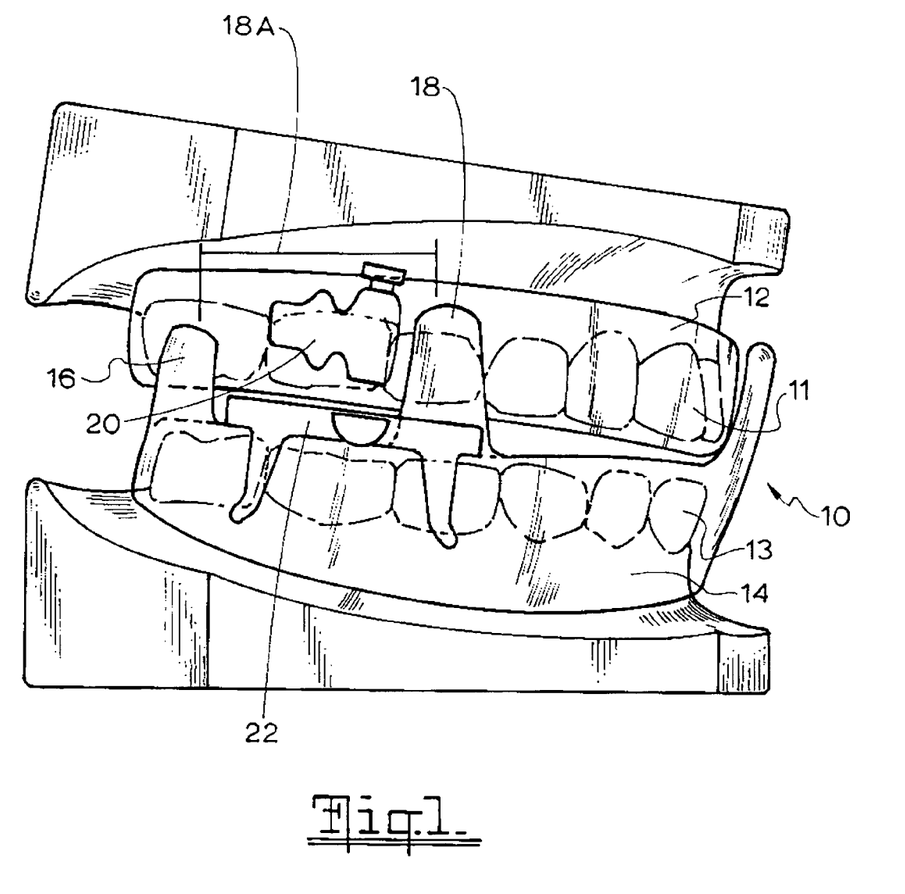
FIG. 1 is a right side view of a mandibular advancement device embodying the present invention located on a model of a patient's teeth and gums.
Figure 2:
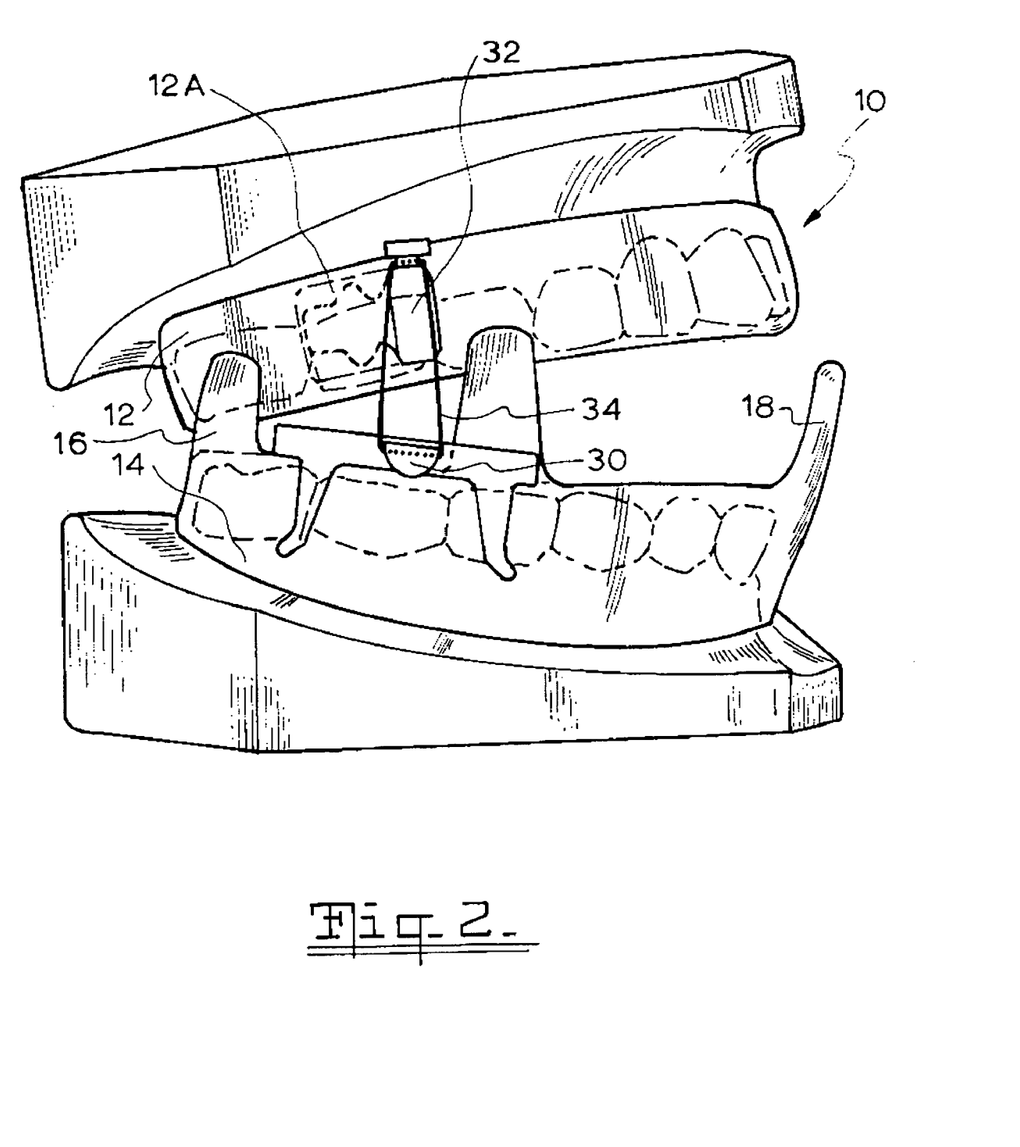
FIG. 2 is a right side view of the device of FIG. 1 illustrating the opening of a mouth wearing the device.
Figure 3:
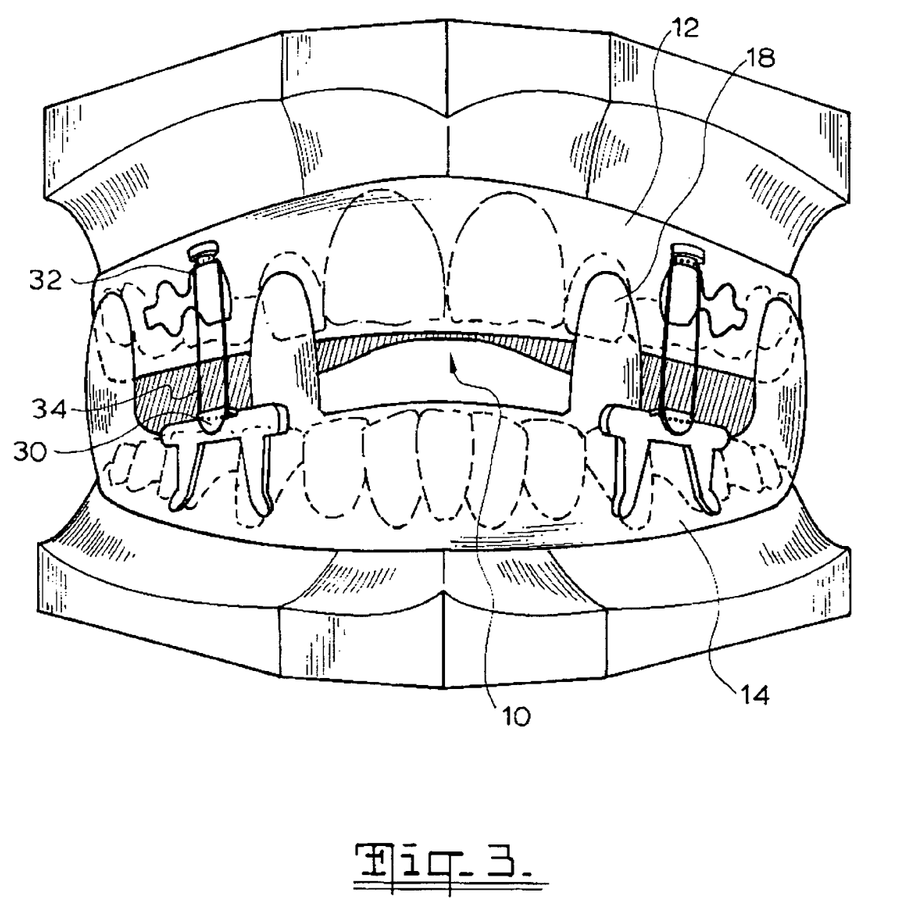
FIG. 3 is a front view of the device of FIG. 1 illustrating the opening of a mouth wearing the device.
Figure 4:
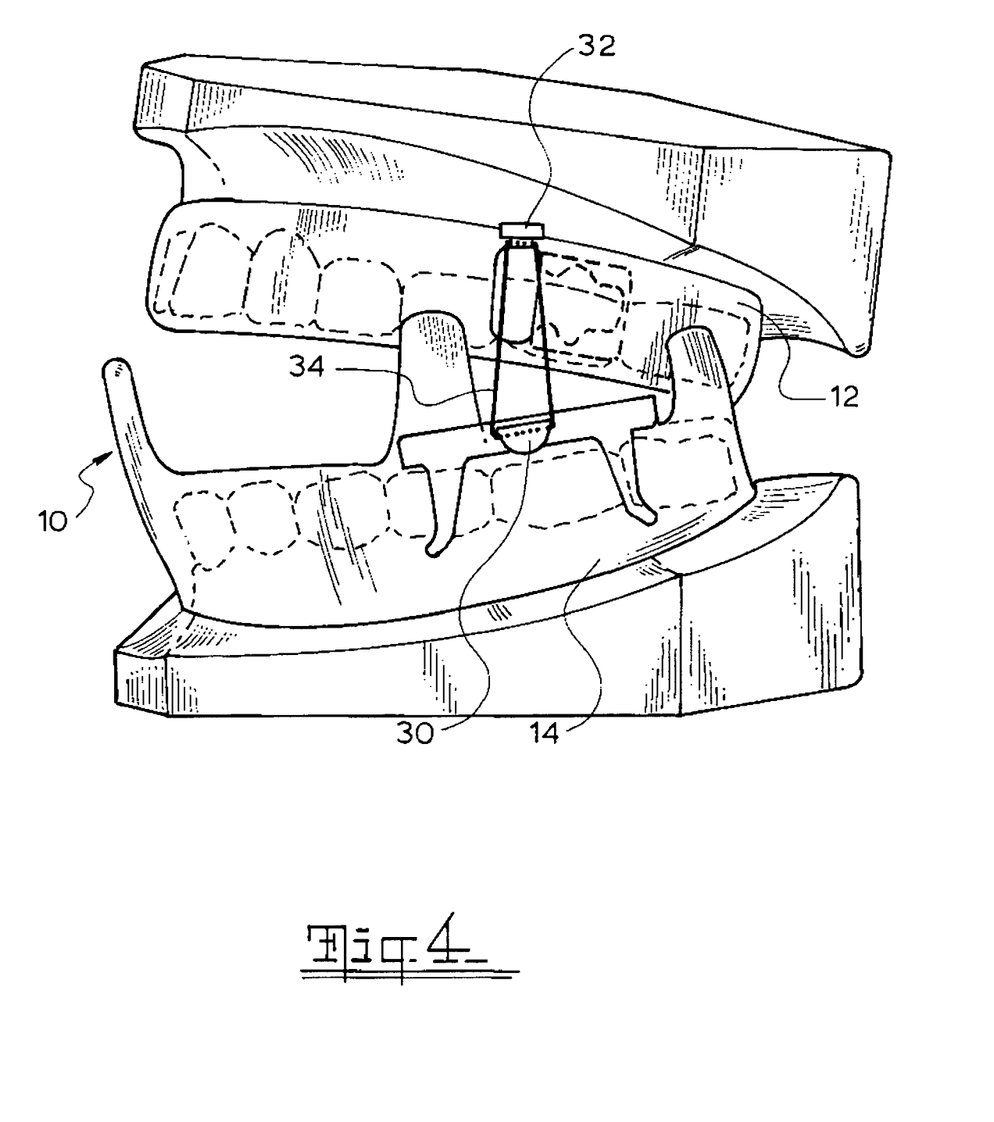
FIG. 4 is a left side view of the device of FIG. 1 illustrating the opening of a mouth wearing the device.

As can be best seen in FIGS. 2, 3 and 4, protrusions 30, 32 are provided on each of the horizontal and vertical inserts 20,22. Protrusions 30, 32 define grooves for attachment of an elastic loop 34 between the protrusions 30 ,32 to encourage the patient to keep his jaws closed when they are asleep, when the patient's muscles relax. The elastics are suitably orthodontic elastics made for 24 hour wear in the mouth.

In use as shown in FIGS. 1-4, when a patient is wearing the lower and upper plates, the horizontal insert 20 locates between the two pairs of pillars 16, 18 when the lower jaw or mandible is in an advanced position. However, the gap between the two pillars allows sufficient freedom of movement to the wearer to move their mandible forwards to a small degree. Thus bite registration or the adjustment of the same is possible while permitting voluntary protrusive movement. The device allows a patient to open their mouth to the extent possible given the advancement of the lower jaw.

In order to manufacture the device, upper and lower impressions are taken of the patients jaws. A measured bite registration is produced. The procedure is similar to that used for taking impressions for other purposes, as is well understood by those in the field, and will not be further described. These items are sent to the laboratory for the construction of the appliance. In the laboratory, the models are duplicated and articulated to the bite registration provided by the dentist.

The freeway space is assessed to decide which vertical component insert 22 is needed to construct the appliance. If the gap is larger than 3 mm then the 3 mm block is used. This allows for an increase or decrease at a later stage after construction, by the dentist, if the bite needs to be altered.

The protrusive position is assessed by using the models, placing them in centric occlusion and marking the position on the upper and lower models. The bite registration is then placed and the protrusive position then marked as a second scribe on the lower model, the difference between these positions providing an indication of how far towards the maximum statistical position the patient's mandible has been moved.

The horizontal insert 20 is then chosen in relation to this measurement. For example, if the patient has been moved 4 mm forward, the practitioner may need to reduce the protrusive position, and is able to do so by up to 5 mm. This decision is metered by the class relationship of the patient as well as the protrusive available to them; a class 2 can protrude more than a class 3 or a class 1. Classes refer to the classification of the three main orthodontic jaw relationships and relate to the maxillo-mandibular jaw relationship.

The vertical displacement insert 22 is set into the lower wax. Following is a preferred positioning protocol:
draw the anterior uplift 18 on the upper model, this is in the distal ⅓ of the canine, and 8 mm distal to that;
look at the upper model topographically, mark the midline raphae, transfer the most distal line to the other side of the arch perpendicular to the raphae, this will be the position of the horizontal component insert 20 on that side;
position the horizontal displacement insert 20 distal to this line and tack into place, then position the vertical displacement insert 22 with the elastic nub not more than 1 mm distal to the leading end of the horizontal displacement insert 20, and scribe a line for each of the legs of this insert 22 to be re-positioned above. Do this on the other side as well;

wax is laid down onto the lower arch and the vertical displacement is checked for bite accuracy;

The vertical displacement insert 22 is placed in the predetermined position, and as close to the lower teeth 13 as possible so it is not out buccally, reducing bulk;

The other side is also placed and the vertical dimension checked again; if there is no other way holes may be ground into the vertical displacement insert 22 so that the vertical dimension is not opened from the prescribed bite. If this needs to be done, the burr used must be sharp and the flash is taken off with the use of a scalpel. Care must be taken not to destroy the fitting legs as they are the retention for the piece in the completed appliance. Set the vertical component 22 to just touch the upper cusps of the articulation, do not damage these cusps, or the fit will be affected, Holes in the upper member 12 are required for the bite to be set confidently, secure the position of the lower vertical displacement inserts 22 with wax;

Lay wax onto the upper and check vertical dimension;

Position the horizontal displacement inserts 20 to their predetermined position, making sure that the midline spine of the insert 20 is in line with the occlusal plane of the arch as assessed to be in line with campers plane of occlusion. Wax down these components and complete the wax up of the upper splint;

lay down the preformed anterior and posterior uplifts 16,18, as predetermined during design and complete lower splint 14. Care must be taken to ensure correct thickness in the anterior uplift 18 and webbing to make the uplift functional without affecting vertical dimension;

The upper and lower splints 12,14 are flasked into an IVO-CAP™ flask; one for each half of the device.

The device 10 is processed in the elastomer.

The device 10 is trimmed after processing, this is achieved with a tungsten carbide burr selection and a selection of abrasive brushes, then a finished glaze is obtained via the use of an appropriate solvent.

The device 10 is checked for fit and accuracy to the bite record once more, the components kit is introduced and the components that match those used to produce the device are placed into the device from the kit The device 10 is sent out with supporting literature and cleaning instructions and a cleaning bath, as well as a set of elastics, and a dentist guide to issuing the device to the patient.

The patient is issued the device 10 at the dental surgery, the fit is checked to the mouth, the bite is assessed by the operator and the patient is instructed in how to insert the appliance and care for it.

An important aspect of the comfort and effectiveness of this embodiment is the manner of use by the patient. The plates 12, 14 do not interact to force the desired advancement—rather, they hold the mandible in the desired advanced position, while allowing for some jaw movement by the user. It is important that the patient is instructed in the correct manner of fitting the device.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

For example, whilst in the embodiment shown the plates 12,14 cover the incisor surface of the teeth 11,13 and the lingual cusps of the posterior teeth, the thickness of the material covering the teeth is very thin typically of the order of 1 mm or less. It is not necessary for the integrity of the plates 12,14 for there to be total coverage so in some places the biting surfaces of the teeth may be exposed.

Further, whilst particular mechanical engagement between the upper and lower plates has been described, the present invention encompasses different mechanical structures including different positioning of pillars, location of vertical and horizontal inserts, and so forth.

The invention claimed is:

1. A mandibular advancement device including
   upper and lower dental plates which operatively fit over at least part of the upper and lower teeth of a user, said upper and lower dental plates being made from a flexible material,
   the lower dental plate having two pairs of spaced apart pillars, each pair consisting of an anterior and posterior pillar, said pairs being on opposing sides of the lower dental plate,
   two removably attachable horizontal displacement inserts, mounted in the buccal region on opposite sides of the upper dental plate,
   two removably attachable vertical displacement inserts mounted in the lower dental plate, placed in a mariner to provide correct vertical registration of the teeth,
   such that operatively each horizontal displacement insert is retained between the respective anterior and posterior pillars to maintain an advancement of the mandible; and
   for each pair of pillars, the separation between the anterior and posterior pillars, relative to the dimensions of said horizontal displacement insert, is such that when said horizontal displacement insert is operatively retained between said anterior and posterior pillars the user is allowed limited freedom of horizontal movement of the user's mandible.

2. A mandibular advancement device according to claim 1, the upper and lower dental plates being formed as separate components, and being operatively connected together by elastic bias which operatively biases said upper and lower dental plates towards one another;
   wherein, operatively, a predefined advancement of the mandible is retained by the device as a result of mechanical interoperation between the horizontal displacement inserts and the two pairs of spaced apart pillars; and
   wherein, operatively, a user is able to move said upper and lower dental plates apart and against said elastic bias by moving the upper and lower teeth apart.

3. A mandibular advancement device according to claim 2, wherein vertical displacement of the upper and lower plates is defined by a dimension and/or position of the vertical displacement inserts.

4. A mandibular advancement device according to claim 3, wherein horizontal displacement of the upper and lower plates is defined by a dimension and/or position of the horizontal displacement inserts.

5. A mandibular advancement device according to claim 2, wherein horizontal displacement of the upper and lower plates is defined by a dimension and/or position of the horizontal displacement inserts.

6. A mandibular advancement device according to claim 1, wherein a dimension of each horizontal displacement insert is selectable from a series of preformed components.

7. A mandibular advancement device according to claim 6, wherein a dimension of each vertical displacement insert is selectable from a series of preformed components.

8. A mandibular advancement device according to claim 6, wherein the plates are formed from a flexible resin which remains elastic.

9. A mandibular advancement device according to claim 1, wherein a dimension of each vertical displacement insert is selectable from a series of preformed components.

10. A mandibular advancement device according to claim 9, wherein the plates are formed from a flexible resin which remains elastic.

11. A mandibular advancement device according to claim 1, wherein the plates are formed from a flexible resin which remains elastic.

* * * * *